(12) United States Patent
Kauvar

(10) Patent No.: US 6,867,007 B2
(45) Date of Patent: Mar. 15, 2005

(54) BINARY OR POLYNARY TARGETING AND USES THEREOF

(75) Inventor: Lawrence M. Kauvar, Mountain View, CA (US)

(73) Assignee: Trellis Bioscience, Inc., South San Francisco, CA (US)

( * ) Notice: Subject to any disclaimer, the term of this patent is extended or adjusted under 35 U.S.C. 154(b) by 0 days.

(21) Appl. No.: 10/427,755

(22) Filed: Apr. 30, 2003

(65) Prior Publication Data

US 2004/0033519 A1 Feb. 19, 2004

Related U.S. Application Data

(60) Provisional application No. 60/377,067, filed on May 1, 2002.

(51) Int. Cl.[7] ............................................... G01N 33/53
(52) U.S. Cl. ........................... 435/7.1; 435/6; 435/7.92; 435/972; 436/518; 436/524; 530/387.3
(58) Field of Search .............................. 435/6, 7.1, 7.5, 435/7.9, 7.92, 91.1, 91.2, 972; 436/518, 524, 528; 530/387.1, 386, 387.3

(56) References Cited

U.S. PATENT DOCUMENTS

| 4,444,879 A | * | 4/1984 | Foster et al. ............... 435/7.95 |
| 4,988,617 A | * | 1/1991 | Landegren et al. ............ 435/6 |
| 5,612,034 A | * | 3/1997 | Pouletty et al. ............ 424/184.1 |
| 6,270,964 B1 | * | 8/2001 | Michnick et al. .............. 435/6 |
| 6,294,353 B1 | * | 9/2001 | Pack et al. ................. 435/69.1 |
| 6,511,809 B2 | * | 1/2003 | Baez et al. .................... 435/6 |
| 2003/0103984 A1 | * | 6/2003 | Kohler .................... 424/178.1 |
| 2003/0157091 A1 | * | 8/2003 | Hoogenboom .......... 424/130.1 |

OTHER PUBLICATIONS

Liu and Chari, "The Development of Antibody Delivery Systems to Target Cancer with Highly Potent Maytansinoids" Exp. Opin. Invest Drugs 6:169–172 (1997).
Melton and Sherwood, "Antibody–Enzyme Conjugates for Cancer Therapy" J Natl Cancer Inst 88(3/4):153–65 (1996).
Sung and van Osdol, "Pharmacokinetic Comparison of Direct Antibody Targeting with Pretargeting Protocols Based on Streptavidin–Biotin Binding" J Nucl Med 36(5):867–76 (1995).

* cited by examiner

*Primary Examiner*—Long V. Le
*Assistant Examiner*—Gary W. Counts
(74) *Attorney, Agent, or Firm*—Morrison & Foerster LLP

(57) ABSTRACT

Effector functions are provided to a desired target with improved specificity by use of two or more complementary targeting components. The targeting components assemble a functional moiety at the target. At the target, the functional moiety itself provides an effector function or binds to additional components which provide an effector function. The effector function may be an enzymatic activity, a label or a signal. The binary or polynary targeting system may be used for analyte determination as well.

25 Claims, 1 Drawing Sheet

BINARY OR POLYNARY TARGETING AND USES THEREOF

CROSS-REFERENCE TO RELATED APPLICATIONS

This application claims priority to U.S. Provisional Application Ser. No. 60/377,067, filed May 1, 2002. The contents of this application are incorporated herein by reference.

FIELD OF THE INVENTION

This invention relates generally to targeting of effector functions to a chosen site with improved specificity based on use of at least binary targeting components, and uses thereof. More specifically, the invention provides methods and kits for cellular targeting which rely on the assembly at the targeted site of a functional moiety from two or more independently targeted components. A variety of effector functions can thereby be provided at the chosen site with higher specificity than is possible for the same effector functions delivered by a single targeting component.

BACKGROUND ART

It has long been recognized that it is, in many cases, desirable to provide a targeted site with a property or function to the exclusion of the environment which surrounds this site. Early examples of such specific targeting include the design of immunotoxins where, in principle, a toxic moiety could be delivered selectively and specifically to a cellular target where the toxicity was desired without negative side effects on the surrounding tissue. It may also be desirable, as further described below, to provide an enzymatic activity at a particular location to the exclusion of the surroundings. Typically, attempts have been made to accomplish this by using a single ligand to carry the active principle to the desired location, relying on the affinity of the ligand for the targeted site to provide selectivity.

However, in many instances, this approach does not confer sufficient selectivity. For example, it has been established that the pharmacokinetics of antibody binding to tumor cells is slow (24–48 hours for maximal specificity). During this time, a toxic effector coupled to the antibody would be expected to have deleterious effects on the remainder of the system. Coupling the antibody against a tumor cell surface antigen to avidin, has been suggested as a way to avoid systemic exposure to toxic effectors. Administering a biotin conjugated toxin or radioligand after the antibody is maximally localized results in clearing of the small molecule from the body in less than one hour, thereby greatly reducing systemic exposure (Sung and van Osdol, *J. Nucl. Med.* (1995) 36(5):867–76).

Similarly, antibody-enzyme conjugates have been used to activate small molecule prodrugs administered after the antibody conjugate has maximally localized (Melton and Sherwood, *J. Natl. Cancer Inst.* (1996) 88(3–4):153–65). This strategy is commercialized by Seattle Genetics, Inc. Enzymatic activation of a prodrug extracellularly is particularly desirable for treating cancer because it creates a bystander effect for killing tumor cells in the vicinity. Thus, the targeting antigen can be as simple as histones, present in large amounts in necrotic cell debris within most solid tumors.

Still another variation of the basic antibody-effector conjugate idea is exemplified by the TAP (tumor activated prodrug) technology commercialized by Immunogen, in which an antibody conjugated to a toxin, e.g., maytansine, is internalized preferentially by cells expressing the relevant antigen for that antibody, with toxin released intracellularly (Liu and Chari, *Exp. Opi. Invest. Drugs* (1997) 6:169–172). A drawback of the TAP approach is that it lacks a bystander effect, thus selecting for mutants that have lost the targeting antigen.

All of these existing techniques suffer from the intrinsic limits on specificity of the targeting antibody. In this aspect, target cells are typically a small fraction of all cells in the body, often in the neighborhood of 1/100,000 or less. Accordingly, even if the antibody has very high specificity, with affinity for target antigen being 100,000 times higher than for any other antigen in the body, the fraction of the conjugated effector that is distributed to non-target cells is still 50%. In practice, antibody specificities are not usually this high, and the background binding is correspondingly higher. Thus, in this context, the use of a single targeting ligand is generally less than satisfactory.

The goal of the present invention is to improve the specificity of targeting in general by requiring multiple independent binding events before an effector function is created. This approach is not limited to delivering effector functions to the surface of cells in vivo, but can also be used to deliver effector functions to intracellular targets, and to cellular or non-cellular targets in vitro.

The invention also provides specific methods and kits for binary or polynary targeting to create an enzymatic activity, of particular utility for activating prodrugs at cell surfaces. The invention further provides methods and kits for assaying an analyte using binary or polynary targeting.

A natural example for binary reconstitution of an effector is the gramicidin toxin, which creates a pore through the cell membrane by end to end dimerization of an ion channel that spans half the width of the membrane. In nature, this particular toxin can flip in the plane of the membrane so it is not necessary to target one monomer to the inside and one to the outside of the cell in order to create the effector function. Although these precedents suggest that the present invention may be embodied in a naturally existing construct, it is normally necessary to alter and/or combine several moieties to make a targeting component with all the requisite properties. The present invention excludes such naturally occurring phenomena.

DISCLOSURE OF THE INVENTION

This invention relates generally to targeting of effector functions to a desired site by means of multiple targeting components. The present method can be used therapeutically, as well as for prognostic and diagnostic monitoring, and for basic research in cell biology. The invention requires at least two targeting components and binary targeting is the preferred embodiment; however, three or more targeting components could also be used. Binary targeting is used in many instances for illustration, without thereby limiting the invention to the binary embodiment.

In one aspect, the present invention provides a method to create an effector function selectively at a desired location. The method can be used, e.g., for visualizing the target, for delivering a drug to the target, for detecting presence of competing analytes, for creating an enzymic activity, and for many other applications. An effector function is created by assembly of individually inactive moieties. The fundamental feature of all embodiments is the provision of two or more targeting components, each of which comprises a targeting portion and a reconstitution portion, wherein the targeting portions bind specifically to distinct sites located in close proximity at the target and wherein the reconstitution portions, when brought into close proximity, assemble into a functional moiety.

The functional moiety may itself provide an effector function, such as an enzymic activity or toxicity. Alternatively, the functional moiety may provide the effector function indirectly by binding to one or more additional materials, such as a toxin or an enzyme.

Thus, in one aspect, the invention is directed to a method to provide a functional moiety specifically to a target which method comprises contacting an environment containing the target with at least two targeting components wherein each of said targeting components comprises a targeting portion and a reconstitution portion. Each targeting portion binds specifically to one of two or more sites located in close proximity on the target. The reconstitution portions, when brought into close proximity, assemble into a functional moiety. As described above, the functional moiety may itself provide an effective function or may bind to one or more additional components which provide such functions.

This method of the invention is adaptable to a variety of applications, including use in vivo to deliver drugs, labels, toxins, or desired components in general to specific targets, use in vitro for the same purpose, and specifically, in a method to assay for an analyte which has the ability to interfere with the formation of the functional moiety.

In another aspect, the present invention discloses a kit to provide a functional moiety, and ultimately an effector function to a target, which kit comprises, in a container, two or more targeting components, each of which comprises a targeting portion and a reconstitution portion. If the reconstitution portions do not generate directly an effector function, additional components which interact with the functional moiety formed by the reconstitution portions may also be included. Preferably, the kit further comprises instructions for using the targeting components and/or the effector to provide an effector function to a cellular structure or other chosen site.

In yet another aspect, the present invention provides a method for competitively assaying an analyte in a sample by assessing the ability of the analyte to interfere with the formation of the functional moiety, for example by to preventing one of the targeting components from reaching the site at which its complementary targeting component is located.

BRIEF DESCRIPTION OF THE DRAWINGS

The drawings are supplied to assist in understanding the invention, and are not intended to be complete or to limit the scope.

FIG. 2(a): the assembled reconstitution portions provide an effector function that has enzymatic activity on substrate (3).

FIG. 2(b): reconstitution portion (1) modulates the enzymatic activity of reconstitution portion (2) on substrate (3), by supplying an allosteric activator.

FIG. 2(c): the assembled functional moiety binds a fluorescent ligand ($3^1$) wherein that binding stimulates emission.

FIG. 2(d): the assembled functional moiety binds an epitope ($3^2$) present on an enzyme (6) naturally, or by epitope tagging, or coupled to the enzyme via an optional linking pair (4 and 5).

FIG. 2(e): the assembled moiety functions as a receptor for a virus ($3^3$).

FIG. 2(f): the assembled moiety constitutes a discontinuous epitope recognized by an antibody ($3^4$) conjugated to an enzyme (4).

MODES OF CARRYING OUT THE INVENTION

Figure 1:
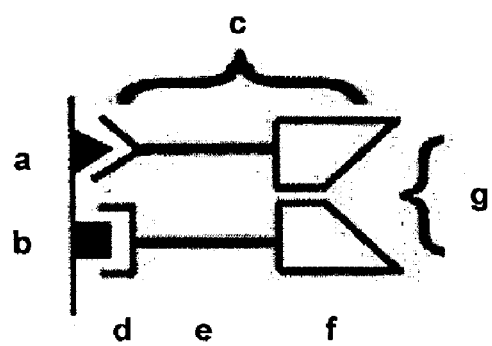
FIG. 1 illustrates the basic concept of the invention. Sites in close proximity (a, b) bind targeting components (c), which comprise a targeting portion (d), an optional linker (e), and a reconstitution portion (f), wherein the reconstitution portions assemble into a functional moiety (g) when brought into close proximity by virtue of the targeting portions binding to the sites in close proximity.
Figure 2:
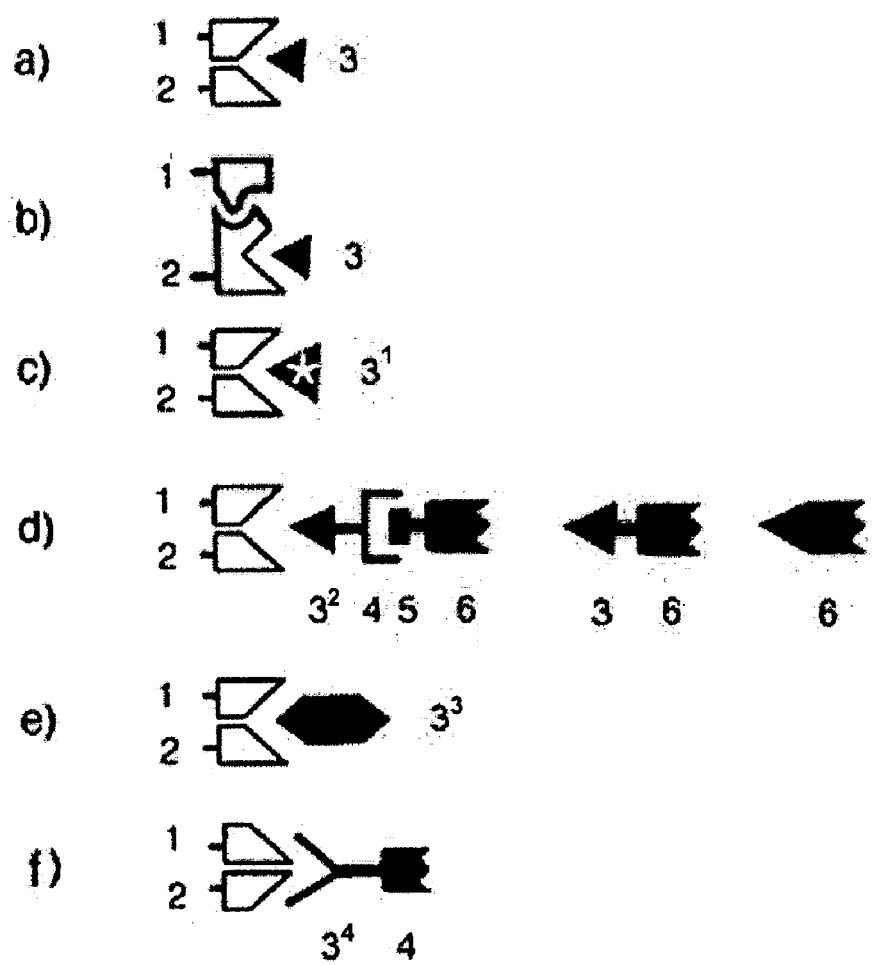
FIGS. 2(a)–2(f) illustrate several formats by which reconstitution portions (1 and 2) can assemble into a functional moiety.

The basic principle of the invention is that independent localization of two or more targeting portions at a single structure can be used to bring attached reconstitution components into molecular scale proximity as needed to form a functional moiety that can itself carry out an effector function or which can couple to additional component(s) to provide an effector function. The combination of a targeting portion and a reconstitution portion constitutes a targeting component.

To be used in the present method, a targeting component must have the following three properties. First, each targeting component must possess a targeting portion to direct the component to the chosen site, either from outside or inside the cell or in vitro. Second, each targeting component must possess, as a reconstitution portion, one piece of a functional moiety, wherein that piece alone does not create the desired function by itself. Third, the targeting components must be capable of assembling a functional moiety at the desired target.

The targeting portions will normally bind to sites in close proximity, with spacing of 5 to 50 nm being preferred. Such sites can be present on a cell surface or on an artificial surface such as a 96-well plastic microplate. The targeting components can also be provided intracellularly, for example using nucleic acid vectors that encode the targeting components.

Targeting components whose targeting portions bind to sites in close proximity at a target are referred to as "complementary". The complementary targeting components may comprise two such components, three such components or four or more such components depending on the nature of the reconstitution portions and location and nature of the proximal sites.

As will be described in more detail below, suitable moieties for use as targeting portions include antibodies, peptides, oligonucleotides, carbohydrates, and other biospecific moieties. Likewise, as detailed below, a wide range of chemical entities can participate as reconstitution portions, including proteins, oligonucleotides, and vitamins. "Reconstitution portion" means a moiety that by itself does not provide a desired functionality but which can contribute to a moiety providing that functionality when brought into close proximity to one or more complementary reconstitution portions. The assembled "functional moiety" can provide an "effector function" by itself. For example, the reconstitution portions can provide an enzymatic activity when assembled. Alternatively, the reconstitution portions can provide a functional moiety when assembled to which an effector can bind. In contrast to the targeting portions, a requirement for each of the reconstitution portions is that it cannot provide the desired function by itself. Rather, two or more reconstitution portions must be brought into close proximity to assemble into a functional moiety. For example, in a preferred embodiment, the variable regions of light and heavy chains of an antibody are used as reconstitution portions, each representing a "demitope" (half of an antigen binding domain, which is known as a "paratope" in the immunological literature). The demitopes are selected such that neither alone can bind a chosen epitope at appreciable affinity, but when brought together, they do form a functional paratope able to bind the chosen epitope.

The targeting portion and the reconstitution portion, which together form a targeting component, can be linked in any suitable manner. A covalent linkage is preferred although sufficiently high affinity non-covalent linkage can also be used. The targeting portion and the reconstitution portion can be prepared separately and then chemically linked, directly or via a short linker. Alternatively, at least one of the targeting components is a fusion protein comprising both a targeting portion and a reconstitution portion.

The targeting components must bind to at least two sites located in distinct positions yet in sufficiently close proximity to enable assembly of a functional moiety. Such distinctly located sites can be the same type, as found in a homodimeric protein for example, or they can be different types, including non-overlapping epitopes on a large protein. The distinct sites can also be on separate molecules that attain close proximity via diffusion, either laterally in the plane of a membrane or in three dimensions. Thus, for example, the necessary proximity may be generated by patching of cell surface receptors. As another example, the necessary proximity may be generated by two independent molecules sharing a similar subcellular targeting property, e.g. by virtue of binding to the same promoter region on DNA or by getting packaged into the same subcellular compartment such as a neurotransmitter synaptic vesicle.

Other terms which may benefit from formal definition are as follows, all technical and scientific terms used herein have the same meaning as is commonly understood by one of ordinary skill in biochemistry, augmented or extended by the following definitions, which are intended to clarify the concepts without thereby limiting the scope of the invention.

"Cellular structure" refers to an intact cell or to a subcellular structure, e.g., nucleus, chromosome, mitochondrion, chloroplast, ribosome, endoplasmic reticulum, Golgi apparatus, lysosome, proteosome, secretory vesicle, vacuole, microsome, or virus. Cells include those from animals, plants, fungi, bacteria, spores, including both natural and recombinant cultured cells. A cellular structure can exist by itself as a separated cell or subcellular structure, or it can exist as part of a higher structure. For example, a subcellular structure can be part of an intact cell, and an intact cell can be part of a multicellular tissue or organ or it can be present together with other cells of the same or different types in a cell culture.

"Immunoglobulin" refers to proteins with sequence homology to canonical immunoglobulin-like domains, i.e., a complex of heavy chains and light chains each composed of a conserved scaffold and one or more variable sequences. "Antibody" is a major type of immunoglobulin, and includes the major forms familiar in the art such as IgG, IgM, IgE among others. However, an immunoglobulin can be a non-antibody molecule, such as MHC molecules and some cell adhesion molecules and cytokine receptors. An antibody moreover can exist in any suitable form, and as used here the term also encompasses any suitable fragments or derivatives. Exemplary antibodies under this wider definition include a polyclonal antibody, a monoclonal antibody, a Fab fragment, a Fab' fragment, a F(ab')$_2$ fragment, a Fv fragment, a diabody (two copies of the same Fv fragment fused), a single-chain antibody and a multi-specific antibody formed from more than one antibody fragment. Certain other standard immunological terminology will also be used in a slightly more general sense. Specifically, a "paratope" refers to the portion of an antibody that binds an antigenic determinant (an "epitope"); a "hapten" is a small molecule epitope, that is normally not immunogenic in mammals unless conjugated to a carrier protein. In the present context, this definition of paratope and epitope extends to analogous recognition elements on non-antibody moieties, including receptors and their ligands.

We have coined the term "demitope" to refer to complementary portions of a paratope in this more general sense; demitope, then, is equivalent in meaning to reconstitution portion, but will generally be used here to highlight an immunological origin for the moiety.

Other antibody-like proteins can also be used to construct either the targeting or reconstitution portions. As previously described by the present inventor and colleagues, it is feasible to mimic the properties of antibodies by embedding hypervariable regions, analogous to immunoglobulin complementarity determining regions, in a scaffold based on a protein other than the basic immunoglobulin scaffold. Specifically glutathione transferase was shown to provide a suitable scaffold for a family of proteins termed "glubodies" (Napolitano et al., *Chem. Biol.* (1996) 3(5):359–67). The use of "antibody" or "immunoglobulin" in the present disclosure, then, is meant to include not only conventional gene encoded IgG's and the like, but also glubodies, fragments of glubodies, and related constructs based on other protein scaffolds, as will be readily apparent to one of ordinary skill in the field of protein structure and function.

"Gene therapy" refers to treatment of a disease by delivery to cells of a functional gene, directly or via a vector that includes a functional gene.

"Prodrug" refers to a pharmaceutically inactive compound that becomes active within the body, either by means of natural chemical changes (e.g. induced by pH changes), or by enzymes normally present in the body, or by enzymes introduced or engineered into the body.

"Exosite modulator" refers to a molecule whose binding to an enzyme, typically but not necessarily at a site spatially distinct from the enzyme's catalytic site, increases or decreases the activity of the enzyme. Allosteric regulators are a special case of this generalized concept, referring to naturally occurring exosite modulators. Similarly, the term exosite modulator for present purposes is intended to include cofactors, which are natural components of an enzyme that are not genetically encoded in DNA but which form a normal part of the enzymatic reaction mechanism, such as metal ions, heme groups, redox or methyl group donors, and the like.

"Epitope tagging" refers to a molecular biology technique in which the gene encoding a protein of interest is mutagenized to include an epitope for easy recognition, e.g. by an antibody. The protein of interest can then be analyzed, isolated or purified via biospecific recognition of the epitope. Exemplary tags known in the art include peptides derived from the myc gene, green fluorescent protein (GFP), haemagglutinin epitopes, and the FLAG peptide. Chemical attachment of a hapten serves the same purpose and for present purposes is also included in the broader sense of epitope tagging.

Construction of Targeting Components

It is possible, although unlikely, that a naturally occurring substance may possess all these properties and thus could be used as a targeting component. For example, the toxin ricin consists of two proteins, one that poisons ribosomes and one that binds a cell surface lectin, promoting cell entry. The two proteins are linked by a disulfide bond. This linkage provides a combination of a targeting portion and an effector portion. Missing from this precedent is the binary targeting aspect of the present invention, since the effector is fully functional as a single moiety.

The linkage between the targeting portion and the reconstitution portion can be a direct chemical crosslink, including disulfide bonds and amide bonds, or it can be mediated by any of the numerous bifunctional linkers known in the literature, including the extensive list in the Pierce Chemical catalog. And of course, the linkage can be intrinsic to the molecule as synthesized, as in a fusion protein or an RNA aptamer fused to a ribozyme. Although covalent attachment is preferred, a sufficiently tight non-covalent linkage can also be used, such as a nickel containing moiety and a hexahistidine nickel-chelating moiety.

Many types of chemical entities can participate as targeting or reconstitution portions. In one embodiment, antibodies provide the targeting portions. For example, two antibodies that bind via their proximal Fab ends to non-overlapping epitopes on a cell surface receptor may be used as targeting portions of two complementary targeting components. To provide the reconstitution portions, the Fc regions are such that they form a discontinuous epitope for which a third antibody is engineered which recognizes this discontinuous epitope. The discontinuous epitope thus is a functional moiety which is able to bind an additional component in turn binds to an effector. Any effector, such as an enzyme, can then be coupled to the third antibody.

In addition to standard antibodies, fragments of antibodies or the related proteins defined above can be used. Other chemical entities can also be used to create targeting portions, alone or in combination. As will be recognized by one of ordinary skill in protein binding assays, an antibody to the EGF receptor can be replaced by EGF itself or a fragment thereof, as an example. Lectins can be targeted to oligosaccharides. Peptide or non-peptide small molecules can be recognized by antibodies or other proteins, as in estrogen receptor and natural or artificial steroids. Other exemplary targeting portions include oligonucleotides, vitamins, lipids, and drugs that bind to specific proteins. All such combinations will be familiar to one of ordinary skill in the art of biospecific recognition.

Sites in Close Proximity

Any multiplicity of distinct sites located in close proximity form the target. In many applications, the sites in close proximity already exist and constitute the target for the formation of the functional moiety and ultimately effector function. For use in vivo, typically, the sites in close proximity already exist either at cell surfaces or intracellularly. Thus, in one embodiment, specific epitopes on a cellular structure, either on a cell surface or inside a cell, are used as the distinct sites to anchor the plurality of the targeting components in close proximity.

Alternatively, an artificial surface can be used to display the distinct sites. For example, two haptens may be conjugated to a single protein or to a latex microsphere in order to capture two targeting components. The distinct sites must be suitable for recognition by the targeting portions of the targeting components, such as a peptide antigen or hapten recognized by an antibody, or a carbohydrate recognized by a lectin, or a nucleic acid recognized by a complementary base pairing sequence. Examples of vitamin-oligosaccharide-, carbohydrate-, lipid-, small molecule-binding substances and structures are known in the art (see e.g. WO 01/02600) and can be used in the present method. The plurality of distinct sites can be of the same or different types.

For example, two protein antigens can be mixed and then immobilized on a polystyrene 96-well microplate or on a nitrocellulose membrane. A protein composed of two different subunits can also provide the distinct sites. Obviously, in all these cases the sites must be spaced sufficiently far apart to avoid steric overlap of the targeting components, but not so far as to eliminate the possibility of assembling a functional moiety from the attached reconstitution portions. Depending on the nature of the sites and targeting components, this spacing will vary, but in general it will be in the range of 5 to 50 nm.

As already noted, there is no intrinsic restriction to only two targeting components. A trimeric enzyme, such as aspirate transcarbamoylase, which achieves functionality via contributions from each monomer could be adapted to the present purpose. Scaffolding proteins, including those with pleckstrin homology domains, or cytoskeletal proteins such as actin may also be used to enable more than two components to contribute to the assembled functional moiety.

If an intact cell is targeted, it can exist independently from a higher structure or it can exist in a multicellular structure or environment, e.g., a tissue or an organ of a multicellular organism, a multicellular organism itself or a cell culture. Non-limiting examples of targetable cells include those from animals, plants, fungi, bacteria, spores, as well as both natural and recombinant cultured cells.

Prior efforts using antibody-enzyme to activate a prodrug has focused on cancer, as a way of increasing the local concentration of drug at the tumor site, which is important given the high systemic toxicity of many cancer drugs. The present invention is not limited to treating cancer, however. Almost every drug can benefit from increased tissue specificity. For example, the invention targeting can be applied to neuroactive drugs with poor penetration of the blood brain barrier, reducing systemic exposure while achieving high concentration for efficient mass action transfer by targeting activation to sites on the barrier.

The cellular structure to be targeted can also be a subcellular structure, present in an intact cell or as a separated component. Among the targetable subcellular structures are nucleus, chromosome, mitochondrion, chloroplast, ribosome, endoplasmic reticulum, Golgi apparatus, lysosome, proteosome, secretory vesicle, microsome, and other vacuoles. Viruses can also be targeted, whether intact or at some stage intermediate stage in the virus life cycle. Intracellular parasites can also be targeted. The following example illustrates targeting intracellular sites. Two demitopes assemble to form a paratope that binds a label. One demitope is fused to an antibody against histones. A library of peptides is conjugated to the complementary second demitope, forming a library of targeting components. If a member of the peptide library induces localization of the targeting component to the nucleus, where the constant anti-histone targeting component is localized, then the two demitopes will assemble a functional paratope, enabling generation of a signal that identifies the library member as having nuclear translocation features. A similar strategy can be applied to other subcellular locations, allowing creation of a repertoire of peptide reagents, or other chemicals, which induce desired localizations. Defects in cell trafficking may thereby be alleviated. For example, the chloride ion channel encoded by the major cystic fibrosis risk factor gene has nearly normal properties as an ion channel but does not traffic properly to the apical end of the cell. Agents that bind to the defective channel and promote its proper localization would be useful therapeutics for cystic fibrosis. Similarly, if the targeting components recognize two transcription factors, then propinquity of the transcription factors on a chromosome can be used to generate a signal or other effector function.

In a preferred embodiment, at least one of the plurality of distinct sites to be targeted is a marker of a biological pathway, such as a signal transduction protein. Other important embodiments include sites contributing to a similar biological function such as the ribosome, as well as sites that define a stage of cell cycle, a cell type, a tissue type, an organ type, a developmental stage, or a disease or disorder.

In a particularly preferred embodiment, the effector function is created on the surface of an intact cell. Effectors that visualize the targeted cell are thereby localized more specifically. Effectors that influence the cell, e.g. by capturing a radioligand or activating a prodrug, also gain specificity for the targeted cell by this means. The cell surface sites can be non-overlapping epitopes on a single protein, or the same epitope on different subunits of a single protein. Different epitopes can also be on proteins that associate by lateral diffusion in the plane of the membrane. The sites can be native to the cell, or engineered into the cell.

Illustrative Reconstitution Portions, Functional Moieties and Effector Functions A variety of embodiments provide the required reconstitution portions of the complimentary targeting components. For example, two demitopes are used to form a paratope as a functional moiety. Preferably, the two demitopes are variable regions of the corresponding heavy and light chains of an antibody. The assembled paratope may then bind a label; for example, to create an effector function enabling visualization of the targeted site. Complementary fragments of a nucleic acid aptamer would be useable in the same manner. Even greater variety of chemical embodiments is useful in instances where the function of the assembled reconstitution portion is simply to display a novel epitope where function is recognition by an antibody or analogous protein. Oligosaccharides would be suitable in this aspect, as would certain lipids, and a wide range of haptens (small molecule epitopes). The discussion below regarding examples of effector functions will provide additional information on the use of nonprotein moieties in a reconstitution portion.

The reconstitution portions of complementary targeting components assemble into a functional moiety which optionally directly provides an effector function, such as enzymatic activity, or the functional moiety can bind an intrinsically active effector function moiety such as a radioligand. The functional moiety thus can bind directly or indirectly an additional moiety that provides the final effector function. For example, the assembled functional moiety can bind directly to an effector, such as an enzyme, or it can bind an epitope, such as biotin, which is attached to the enzyme. Engineered epitopes, such as myc or FLAG can be introduced into the effector enzyme using established epitope tagging technology, allowing it to be captured at the site of a reconstituted paratope that binds this motif. Further, the assembled functional moiety can be coupled to the final effector via a linking system such as a pair. Any suitable linking pair can be used in this setting, e.g., biotin and avidin; or a FLAG epitope and an antibody that binds to the FLAG epitope; or a nickel-containing moiety and a hexahistidine nickel-chelating moiety. For example, the assembled reconstitution portions can bind a ligand conjugated to biotin which in turn is bound to avidin conjugated to an enzyme. Such "sandwich" constructs are well established in the immunological literature.

Applications

The method of the invention and the targeting components which are useful therein can be adapted to a wide variety of applications. In one illustrative application, the method is applied in gene therapy and related research.

The effector functions are provided by antisense sequences, small interfering RNAs, peptide nucleic acids, sequence specific polyamides, or a virus that carries a gene therapy/regulatory payload. The effector function is provided inside a viral particle. A functional receptor site for that viral particle is provided on a cell surface by construction of appropriate proximal sites, or by appropriate design of targeting portions. If the virus is non-infectious to human cells, e.g., an insect virus, there is a low background for gene vector insertion into human cells. The targeting portions may be antibodies against natural cell surface receptors, allowing creation of a novel receptor for the xenotropic virus, with the high specificity that arises from binary targeting. It has been shown that a single chain antibody against hoof and mouth virus, when fused to a cell surface protein (ICAM1), functioned as a novel receptor for the virus, allowing high infectivity with respect to cells displaying ICAM1 that previously were not susceptible to the virus (Rieder et al, PNAS (1996) 93:10428–10433). According to the present invention, the paratope recognizing the virus is dissected into two complementary demitopes, each fused to ICAM1 and expressed by cells. Association of ICAM1 molecules by lateral diffusion in the cell membrane creates a receptor for the virus.

The invention method may also be used to label specific targets. The effector function is thus a labeling moiety. Exemplary labeling moieties include chemical, enzymatic, radioactive, phosphorescent, fluorescent, fluorescence-quenching, luminescent and fluorescence resonance energy transfer (FRET) labels, as well as microspheres containing dyes of various sorts. The labeling moiety can generate a detectable signal, enhance an existing signal, or quench or weaken an existing signal. In a preferred embodiment, the labeling moiety generates an immediately detectable signal, e.g., fluorescence quenching, fluorescence enhancement, or an alteration of NMR spectrum. Examples of such interactions are described in the literature. For example, Kranz et al., *Proc. Natl. Acad. Sci. USA* (1981) 75:5807–5811 took advantage of the ability of assembled antibody variable regions to quench the fluorescence of bound fluorescein, by more than 90%, in order to monitor immunoglobulin recombination and active site formation. Thus, fluorescence quenching is a practical way to monitor reconstitution (active site formation) upon mixing resolved heavy and light chains. Applied to the invention method, the heavy and light chains are the demitopes and the resulting associated combination is the functional paratope which, upon binding fluorescein, provides an immediate signal, namely fluorescence quenching. The system of Kranz is adapted to the method of the present invention by coupling the light chain with a first targeting portion and the heavy chain to the second, complementary targeting portion.

Rothstein et al., *Mol. Immunol.* (1983) 20:161–168 used a similar phenomenon, that of fluorescence quenching of p-azophenylarsonate by various anti-idiotypic antibodies, as a measure of affinity of the antibody for the dye. The higher the affinity, the more reconstituted paratopes that are formed, and hence the greater the degree of fluorescence. The phenomenon of fluorescence quenching by binding to a paratope is not limited to organic fluorescent molecules. Metal-based complexes may also exhibit quenching upon sequestration in organic environments, such as by binding to antibodies or assembled receptors. For example, fluorescence quenching of rubidium complexes occurs upon binding to antibodies raised against such complexes (Shreder et al., *J. Am. Chem. Soc.* (1996) 118:3192–3201).

The immediate signal generated may not necessarily involve quenching of fluorescence, but may, depending on the fluorophore and the paratope, be fluorescence enhancement. For example, as shown by Parker et al., *Biochemistry* (1967) 6:3417–3427, antibodies raised against dansyl-lysine effect a 150-fold enhancement of the fluor's emission upon binding. Other examples of fluorescence altered by environment include "Quantum Dots" which are clusters of metal atoms. Their fluorescence properties are greatly enhanced and tuned to a narrow emission frequency by appropriate molecular environments (U.S. Pat. No. 6,207,392; Bruchez, et al., *Science* (1998) 281:2013–2016). Similarly, the NMR properties of compounds are often influenced by their environment, specifically their ability to interact with water molecules. For example, a protease assay has been described which is based on enzymatic cleavage of a gadolinium containing compound to expose the metal to water, thereby drastically changing the NMR spectrum (Moats et al., *Angew. Chem. Int. Ed. Engl.* (1997) 36:726). Similarly, a radio-opaque compound can be captured, for imaging by X-ray or CAT scan technology. A compound showing high reflectivity for ultrasound can likewise be captured.

In another application, the invention method may be used to inhibit the cell cycle of any intact cell, or otherwise damage or cause death of said cell or surrounding cells. Any suitable effector can be used for such cell growth inhibitory, damaging or eradication function, such as a radioactive moiety, a toxin or a prodrug which will be coupled to the functional moiety formed by the reconstitution portions. (For treating tumors, the targeting portion on each targeting component could be an antibody against histone, which is present in cell debris of necrotic tumor foci.)

In another application, the present invention provides for a method to create an enzymatic activity, for example on a cell surface or in a diagnostic 96-well microplate. In one specific embodiment, the reconstitution portions comprise fragments of an enzyme that are inactive separately but which reconstitute catalytic activity when assembled as a consequence of co-localization of the targeting components. Examples of such direct formation of enzymatic activity have been disclosed (U.S. Pat. Nos. 5,643,734 and 6,270,964). In those prior art examples, the reconstitution event was used to establish whether moieties attached to the reconstitution portions interact with each other, rather than to effect targeting.

Two additional formats for creating enzymatic activity at a specific target by employing methods similar to those disclosed in U.S. Pat. Nos. 5,643,734 and 6,270,964. In the one format, the two reconstitution portions are assembled to form an epitope recognition moiety, and an enzyme displaying the relevant epitope is thereby bound to the assembled structure, thus providing an enzymatic activity. A variation of this approach uses a linking pair as described above. For example, if the epitope recognized has biotin attached, then the enzyme can be coupled to avidin and thereby associated with the reconstituted moiety. Likewise, the assembled reconstitution portions can generate a discontinuous epitope recognized by an antibody, and the enzyme can be coupled to that antibody. The common feature in all these variations is that the assembled functional moiety captures an enzyme as an effector function.

In a second format, one of the reconstitution portions comprises an exosite modulator for an intact enzyme, which then acts as the complementary reconstitution portion. Upon reconstitution, therefore, the effector function is formed directly as the enzymatic activity is immediately either induced or suppressed. Naturally occurring allosteric sites can be used in this way as can non-natural sites, discovered by molecular biological or combinatorial chemistry techniques (Dennis et al., *Nature* (2000) 404:465–470). In a variation of this format, one of the reconstitution portions comprises a necessary cofactor for an enzyme, such as NADH, and the other demitope comprises an enzyme or a functional fragment thereof, whereby upon reconstitution, the enzymatic activity is activated; thus, the reconstitution portions are based on the approach set forth in the Apo-Enzyme Reactivation Assay (ARIS), in which the co-factor FAD is coupled to an analyte (Dosch et al. *Fresenius J. Anal. Chem.* (1998) 361:174–178). An enzyme such as glucose oxidase that uses that cofactor is catalytically inactive if the analyte-cofactor is sequestered by virtue of binding to an antibody; if analyte is introduced which competes for the antibody binding site, then the co-factor becomes available and the enzyme is activated.

In still another variation, one of the reconstitution portions comprises an inhibitor of an enzyme that serves as the other reconstitution portion, whereby upon reconstitution, the enzymatic activity is inhibited. Alternatively, one of the reconstitution portions can provide a high affinity binding site for a flexible flap that occludes or occupies the catalytic site of an enzyme which then serves as the other reconstitution portion, whereby upon reconstitution, the enzymatic activity is activated. Such flaps are well known, e.g., the Protein Kinase C pseudosubstrate sequence that occludes the enzyme active site until a conformational change in the protein is triggered. Alternatively, one reconstitution portion can supply a pseudosubstate type inhibitor of activity (Zhong, et al., *J. Biol. Chem.* (1999) 274(48):33913–20). The common feature of all these variations is that the activity of an intact enzyme is modulated by the second reconstitution portion. The created enzymatic activity can be used for any suitable purpose, including generating a signal or activating a prodrug.

The present invention can also be used to assay an analyte in a sample. In one embodiment, at least a first targeting portion recognizes both the analyte itself and an analog of the analyte immobilized on a surface. Exemplary surfaces include the surface of a microplate, a glass slide, a test tube, a nitrocellulose membrane, a latex or other plastic bead, a colloidal gold particle, a colored particle, a magnetic bead and a quantum dot. The analog can be the analyte itself in an immobilized form, or a closely related molecule, or it could be any substance cross-reactive with regard to the relevant targeting portion; all of these are considered analogs of the analyte for present purposes. A second targeting component is able to bind to a site in close proximity to the analyte-occupied site in order to generate a signal. Any signal moiety can be used, including an enzyme, a radioactive moiety, a fluorescent or phosphorescent moiety including microspheres, and an NMR detectable moiety. Analyte in the sample to be tested competes with the analyte-occupied site for the first targeting portion. In this manner, any analyte can be assayed which is recognized by at least said first targeting portion, by assessing the presence or amount of diminution of the signal effected by the sample in comparison to a control lacking analyte.

Exemplary analytes include a peptide, a protein, an oligonucleotide, a nucleic acid, a vitamin, an oligosaccharide, a carbohydrate, a lipid, a small molecule and a complex or combination thereof. The benefit of binary targeting in this instance is maximized if the analyte is one for which a therapeutic binary targeting system is available. That is, in an analytical context, many candidate therapeutics can be tested against a tumor specimen, for example, to determine which pair of targeting components is most likely to deliver an effector function with high specificity to the tumor. If a sufficient sample of tumor cells is available, then the candidate pairs can all be tested directly, using a signal generating effector. However, if sample quantity is limited, or if it is desired to detect cell free tumor antigen shed into the blood or urine, then the competitive assay analogous to that described above is more appropriate than a direct assay.

Kits

The invention also provides kits constructed to provide a functional moiety and/or an effector function to desired target. Each kit comprises, in one or more containers, two or more targeting components. Each targeting component comprises a targeting portion and a reconstitution portion as described. The reconstitution portions may provide an effector function when assembled, or may result in a functional moiety that is able to couple to an effector function. The kit may, in the latter case, contain additional components to provide the effector function. Preferably, the kit further comprises instructions for use. One preferred kit enables creating an enzymatic activity at a cell surface by means of binary targeting, for diagnostic imaging or therapeutic treatment of a targeted cell type.

Illustrative Specific Embodiments

The specific embodiments described below are intended to illustrate the utility of the present invention, and are not intended to limit its definition. As will be apparent to one of ordinary skill in the art of biochemistry, the invention can be embodied in a wide range of chemical entitites, all sharing the key feature of multiple independent targeting components, which provide improved specificity for bringing an effector to a chosen site as compared to the same effector delivered by a single targeting component.

Preparation A

Construction of Targeting Components

A convenient method to obtain targeting components is described. Single chain antibodies (scFv) are small immunoglobulin-like molecules that contain variable regions derived from antibody heavy and light chains coupled through a linker. These constructs are screened using standard phage display techniques (Marks et al., *New England J. Med.* (1996) 335:730–733). A multiplicity of candidate paratopes is thereby provided, from which several are selected which bind an effector, such as biotin or dansyl-lysine. Once appropriate paratopes are identified in this manner, the linker between the heavy and light chain derived variable regions is cleaved at the DNA level to obtain the demitopes, which can be further mutagenized so as to weaken their intrinsic attraction for each other in the absence of linked targeting portions. Similarly, phage display of scFv antibody-like constructs can be used to isolate the targeting portions of the targeting components. A targeting component is then created by chemically linking a targeting portion to a demitope, or by fusing the encoding sequences at the DNA level.

EXAMPLE 1

Imaging of Tumor Cells

Tumor cells expressing the EGF receptor are imaged following construction of proteins with two subunits, each consisting of two domains analogous to the constant and variable domains that make up an antibody Fab fragment (represented as $C_H$-$V_H$::$C_L$-$V_L$). The $V_H$::$V_L$ portion that binds antigen is normally called a paratope, and the separated $V_H$ and $V_L$ portions will be referred to here as demitopes. Copending application, Ser. No. 10/071,844 filed Feb. 8, 2002, incorporated herein by reference, describes replacing the constant domains ($C_H$::$C_L$) with any proteins (X and Y) that bind to each other. The paratope ($V_H$::$V_L$) thereby formed by the attached variable regions provides a means of detecting the X::Y interaction. In the present example, the X and Y portions are comprised of proteins, such as single chain Fv antibodies, that bind non-overlapping epitopes on the EGF receptor. The resulting signal generated as a result of the assembly of a functional paratope provides higher specificity for visualizing the targeted cell than is feasible with a single targeting component coupled to a signal generating moiety. That is, if X and Y individually have 1,000:1 preference for their target antigens over other antigens in the body, and are independent in their binding, then the X::Y specificity is ~1,000,000:1. The captured ligand is the fluorescent hapten dansyl-lysine, whose emission is stimulated 150-fold upon binding, allowing detection in an in vitro diagnostic setting. Alternatively, the captured ligand is a compound with a gadolinium atom exposed to water until bound to the assembled paratope. The change in NMR signal when bound as compared to when free in solution thereby enables magnetic resonance imaging of tumor cells inside the body.

EXAMPLE 2

Drug Delivery

Similar constructs are used to deliver a therapeutic effector to the targeted tumor cells. Specifically, the assembled paratope is chosen for its ability to bind to biotin. A biotin conjugated radioligand or a biotin conjugated prodrug activating enzyme then provides the therapeutic effector. The prior art has described the pharmacokinetic advantages of introducing small molecule final effectors after the targeting proteins have maximally localized. Binary targeting preserves those advantages while enabling higher specificity in the protein targeting aspect of the technique.

EXAMPLE 3

Facilitating Virus Entry

The paratope created by the targeting components constitutes a receptor for an insect virus that is non-infectious to normal human cells. The reconstituted receptor enables a very low background for gene therapy vector insertion into human cells. Feasibility of introducing novel viral receptors into cells is established by the prior art, in which a single chain antibody against hoof and mouth virus was isolated; when fused to a cell surface protein, the antibody functioned as a novel receptor for the virus, allowing high infectivity for cells that previously were not susceptible to the virus (Rieder et al., *Proc. Natl. Acad. Sci. U.S.A.* (1996) 93:10428–33).

EXAMPLE 4

Analysis of Nuclear Localization

This example illustrates binary targeting of the nucleus using one targeting component known to bind thereto and a second targeting component containing, as the targeting portion, a peptide whose ability to localize to the nucleus is to be tested. The method takes advantage of the presence of histones in the nucleus, so that a targeting component where the targeting portion is an antibody to histones is known to be localized thereto. Thus, an antibody to histones is conjugated to a first demitope. A library of peptides to be tested for localization is conjugated to the complementary second demitope as targeting portions. Cells are engineered by standard methods so as to express the anti-histone:demitope-1 construct and one member of the peptide library with its attached demitope-2. The assembled paratope is labeled so as to generate a signal by stimulating fluorescence of dansyl-lysine. A peptide that induces localization to the nucleus generates a signal since the signal is only generated if the peptide brings the attached demitope-2 into close proximity to demitope-1.

What is claimed is:

1. A method to provide a functional paratope to a target, which method comprises:

a) providing two or more complementary targeting components, each of said targeting components comprising a targeting portion and a demitope wherein each said targeting portion binds specifically to one of two or more sites located in close proximity on said target and wherein the binding of the targeting portion to the target brings the demitopes in close proximity wherein said demitopes, when brought into close proximity, assemble into a paratope functional at said target; and b) contacting said complementary targeting components to an environment comprising said target thereby, inducing assembly of said paratope functional said target.

2. The method of claim 1, wherein said paratope directly or indirectly binds an effector.

3. The method of claim 1, wherein the targeting portions are peptides, proteins, oligonucleotides, nucleic acids, vitamins, oligosaccharides, carbohydrates, lipids, haptens, or a complex or combination thereof.

4. The method of claim 3, wherein the targeting portions are immunoglobulins or fragments thereof.

5. The method of claim 4, wherein the immunoglobulins or fragments are independently polyclonal antibodies, monoclonal antibodies, Fab fragments, Fab' fragments, $F(ab')_2$ fragments, Fv fragments, diabodies, single-chain antibodies or multi-specific antibodies formed from antibody fragments.

6. The method of claim 1, wherein the target is a cellular structure.

7. The method of claim 6, wherein the cellular structure is an intact cell.

8. The method of claim 6, wherein the cellular structure is a subcellular structure.

9. The method of claim 1, wherein the targeting portions and the demitopes are covalently linked directly or by a linker.

10. The method of claim 1, wherein at least one of the targeting components is a fusion protein.

11. The method of claim 2, wherein the paratope binds to a label.

12. The method of claim 11, wherein the label generates an immediately detectable signal.

13. The method of claim 2, wherein the paratope binds to an effector that carries out its effect on the surface of a cell.

14. The method of claim 2, wherein the effector that binds to the paratope is a peptide, a protein, an oligonucleotide, a nucleic acid, a gene therapy or gene regulatory construct, a virus that carries a gene therapy/regulatory payload, a prodrug, a toxin, a radioactive moiety, a NMR detectable ligand or a fluorescent or phosphorescent ligand.

15. The method of claim 14, wherein the effector that binds to the paratope is an enzyme.

16. The method of claim 2, wherein the paratope binds an effector directly.

17. The method of claim 2, wherein the paratope binds an effector indirectly by a separate linking pair.

18. The method of claim 17, wherein the separate linking pair comprises:

a) biotin and avidin or streptavidin; or b) a FLAG epitope and an antibody that binds to said FLAG epitope.

19. The method of claim 1, which is conducted intracellularly.

20. The method of claim 1, which is conducted in vivo.

21. The method of claim 1, wherein the distinct sites located in close proximity on the target are different regions of a single molecule.

22. The method of claim 1, wherein the distinct sites located in close proximity on the target are located in separate molecules that can attain close proximity by diffusion, either laterally in the plane of a membrane or in three dimensions.

23. A kit to provide an effector to a target, which kit comprises, in one or more containers, two or more complementary targeting components, each of said targeting components comprising a targeting portion that binds specifically to one of two or more distinct sites located in close proximity on a target and a demitope, wherein said demitopes, when brought into close proximity, assemble into a paratope on said target.

24. The kit of claim 23, which further comprises an effector which interacts with or binds to said assembled paratope.

25. The kit of claim 23, which further comprises instructions for using the targeting components.

* * * * *